United States Patent [19]

Daroczy et al.

[11] 4,430,164
[45] Feb. 7, 1984

[54] FAULT-COMPENSATING ELECTRO-ANALYTICAL MEASURING PROCESS AND EQUIPMENT

[75] Inventors: Janos Daroczy; Janos Erdelyi; Jeno Havas; Lajos Kecskes; Henrik Müller, all of Budapest, Hungary

[73] Assignee: Radelkis Elektrokemiai Müszergyarto Szövetkezet, Budapest, Hungary

[21] Appl. No.: 353,290

[22] Filed: Mar. 1, 1982

[30] Foreign Application Priority Data

Mar. 26, 1981 [HU] Hungary ................................. 758

[51] Int. Cl.$^3$ ............................................. G01N 27/30
[52] U.S. Cl. ................................. 204/1 T; 73/1 R; 204/401
[58] Field of Search ............... 204/401, 415, 416, 417, 204/418, 419, 420, 1 T; 73/1 R

[56] References Cited

U.S. PATENT DOCUMENTS 4,167,163  9/1979  Möder ............................ 204/401 X
4,189,367  2/1980  Connery et al. ..................... 204/401

Primary Examiner—G. L. Kaplan
Attorney, Agent, or Firm—Gabriel P. Katona

[57] ABSTRACT

An electro-analytical measuring process and apparatus for the determination of the concentration and the ion-activity of stationary or flowing solutions or of the partial pressure of gases. The measuring cell of the measuring equipment—connected to an electronic signal processor—comprises, in addition to one or several sensing elements and reference electrodes, at least one fluid clutch capable of galvanically short-circuiting one or more parts of the measuring chain. The measuring cell of the measuring equipment comprises, in a given case, integral sensing unit and standardizing media, being in contact with sensing element. Further, a control unit for programming short-circuiting belongs to the measuring cell, a fault compensating unit producing signals is connected to the control unit—for calculating the value of the parameter to be measured—is connected to the output of the fault compensating unit.

5 Claims, 3 Drawing Figures

FAULT-COMPENSATING ELECTRO-ANALYTICAL MEASURING PROCESS AND EQUIPMENT

BACKGROUND OF THE INVENTION

The present invention relates to an electro-analytical measuring process and apparatus for the selective, rapid and high-precision determination of the concentration and the ion-activity of stationary or flowing solutions or of the partial pressure of gases.

It is well known that an electro-chemical measuring chain is composed of several parts—sensing element or elements and reference electrode or electrodes. Consequently, the measuring signal obtained at the relevant outputs of the measuring chain appears as the resultant of several current or voltage signals, generally as an algebraical amount. Consequently, in the case of some undesirable change, a disturbance occurs at any of the elements of the measuring chain arranged in a measuring cell of traditional construction, resulting e.g. from thermic or "aging" reasons, this cannot be distinguished from the range of the signal incurring as a result of the change of the parameter to be measured, e.g. increase or decrease of the sample-concentration.

Obviously, traditional measuring techniques calibration, standard addition, setting of the constant ion-intensity, programming of slope, etc., see e.g. Havas: Ion and molecule selective electrodes in biological systems and latest results of chemistry, published by: Akadémiai Kiadó in 1980, pages 80 to 87 do not strive, since they cannot strive to determine the extent of the fault-signal resulting from the disturbances already mentioned. All things considered, the methods known till now may be attributed to the comparison of the relevant electro-chemical parameters of the sample and of one or more liquids, standard solution or gas, of a known composition. It means that before the measurement is carried out, the electronic behavior of the measuring equipment and the electrochemical behavior of the measuring equipment and the electrochemical behavior of the measuring cell are to be harmonized—this is called; matching.

As a consequence of the uncontrollable irregularity of the disturbances occurring, the accuracy of the measurements depends obviously on the frequency of the above matching or matchings. In precision measurements it is required to carry out some matching prior to each and every measurement—at least for the sake of control. If the time necessary for the indispensable flushing of the measuring cell is also considered, the total period of the analysis will be—in the case where two standard liquids are applied—approximately five times more than the actual period of the measurements. Though by "one-spot" matching wide spread in electro-analytics this period may be reduced to one half, there is a fault resulting from the interim change of the response-function slope of the measuring cell that cannot be eliminated.

The incidental fluctuation of the electro-chemical parameters of the measuring cell is not the only reason for frequency matching. This is required also for the reason that the long-time stability of the measuring equipment cannot be unlimited because of principle-electro-analytical reasons.

It is obvious from the above that the total period of the precision analysis is considerably long—because of the matching steps between factual measurements. On the other hand, it is impossible to carry out continuous, and at the same time high-precision measurements, as the construction of traditional measuring cells does not factilitate the determination of the fault signals during measurement, not speaking of matching to be performed simultaneously with the measurement.

SUMMARY OF THE INVENTION

The electro-analytical measuring process according to the present invention is based on the recognition that in the case where at least one part of a measuring cell comprising a sensing element or elements and reference electrodes, arranged in a measuring cell suitable for performing intermittent, intermittently continuous or continuous measurements is galvanically, periodically short-circuited, the measuring signals obtained in the short-circuited states, provide characteristic values as to the electro-chemical behavior of the non-short-circuited parts of the measuring cell and to their incidental interim changes and thus they afford the elimination of disturbances resulting from said changes.

The measuring cell of the electro-analytical measuring apparatus comprises a measuring cell and electro-galvanic signal processor joined to it and according to the present invention comprises at least one sensing element and reference electrode, further, at least one means capable of galvanic short-circuiting of one or several parts of the measuring cell—preferably a high-condutivity fluid, current, clutch, filled, in given cases, with electrolyte of various concentrations. By this, it is possible to compensate the disturbing effects occurring in the electro-chemical behavior of non-short-circuited parts of the measuring cell.

A further recognition according to the present invention is that the compensation of the disturbing changes of further electro-chemical features, e.g. asymmetrical potential and response-function slope, can be also carried out in the case where the measuring cell comprises an "integral sensing element" constituting the subject of another invention of the present inventors.

The continuous or intermittently continuous flowing of one or more of the standardizing media serves to eliminate the disturbing effect of the flowing potentials arising in the course of continuous or intermittently continuous measurements.

A further preferred embodiment is one in which the composition of the reference electrodes, standard solutions and the internal electrolytes between the standard solutions and/or the sample is the same or nearly the same as the composition of the standard-solution and the sample in contact with them, aims at eliminating the disturbing effect of the diffusion potentials.

As the measuring signal provided by the measuring cell should be determined both in the short-circuited and non-short-circuited state—preferably by turns—, in a preferred embodiment of the measuring equipment a control unit is also joined to the measuring cell, controlling, according to a prescribed program, the periodical galvanic short-circuiting of one or several parts of the measuring chain.

In an embodiment aiming at utilizing further advantages resulting from the possibility of automatization, a fault compensating unit is joined to the electronical signal process and to the control unit controlling, according to a prescribed program, fault compensating signal or signals from the measuring signals obtained in the short-circuited, i.e. non-short-circuited state of one or more parts of the measuring chain.

Finally, in a completely automated embodiment, the apparatus comprises an arithmetic unit—calculating the value of the parameter to be measured by utilizing the fault compensating signal or signals—joined to the output of the fault compensating unit and thus it calculates itself the value of parameters to be measured, free of disturbing effects.

The electro-analytical measuring process and apparatus according to the present invention are illustrated in the attached figures and examples, without limiting the patent claims to those described above.

DETAILED DESCRIPTION OF THE INVENTION

Figure 1:
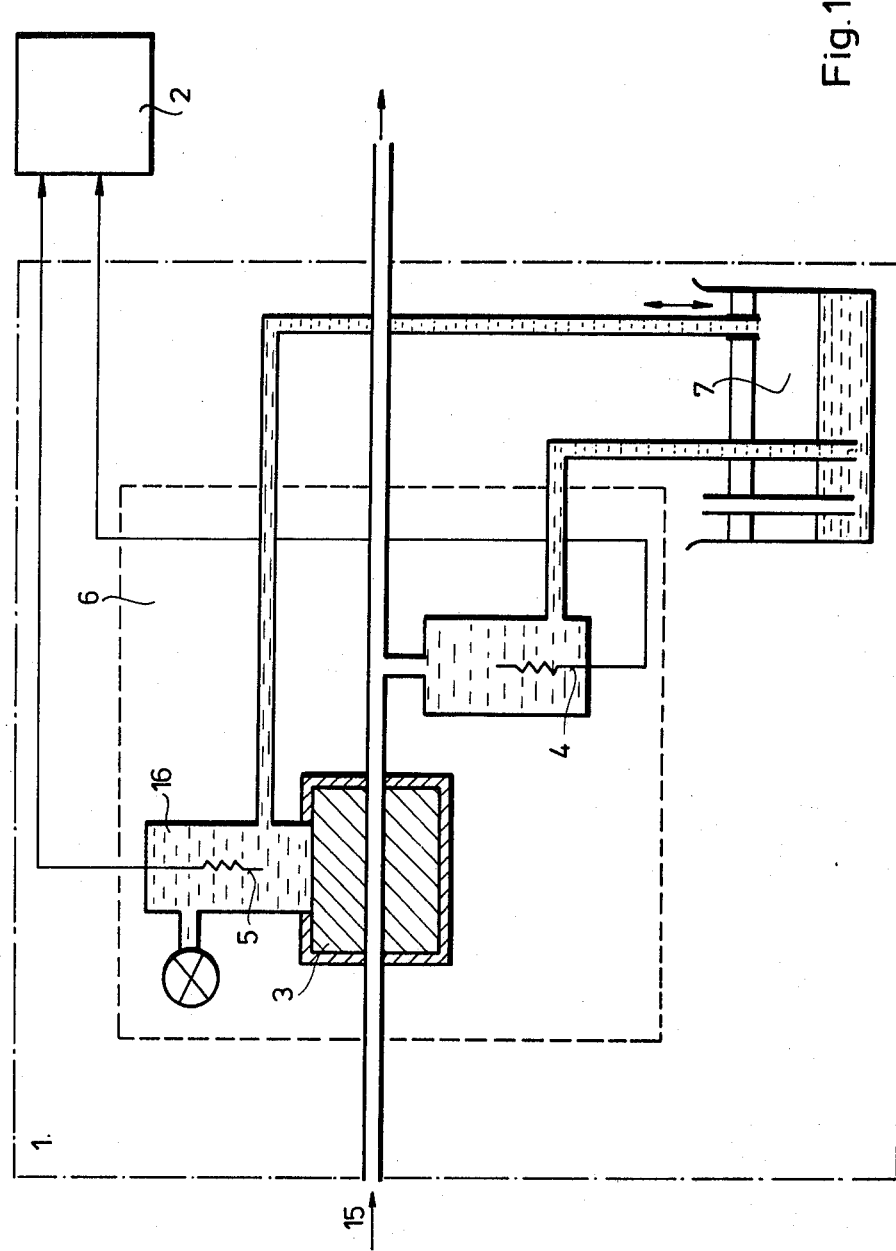
FIG. 1 shows a simple fault-compensating pK measuring apparatus with measuring cell, provided with fluid clutch.

In the FIG. 1 measuring cell is connected to electronic signal processor 2. In measuring cell 1, sample 15 is in contact with sensing element 3 and sample-side reference electrode 4. Besides sample 15, sample-side reference electrode 4 and sensing element 3, measuring chain 6—including traditional elements of measuring cell 1—comprises sensing-element-side reference electrodes 5 as well, being in galvanic contact with sensing element 3 through internal electrolyte 16. In addition to measuring chain 6, measuring cell 1 comprises fluid clutch 7 connected galvanically to liquid spaces of sample-side and sensing-element-side reference electrodes 4 and 5 through a liquid duct. Measuring cell 1 is connected to electronic signal processor 2 through sample-side and sensing-element-side reference electrodes, 4, 5 constituting two "ends" of measuring chain 6.

Figure 2:
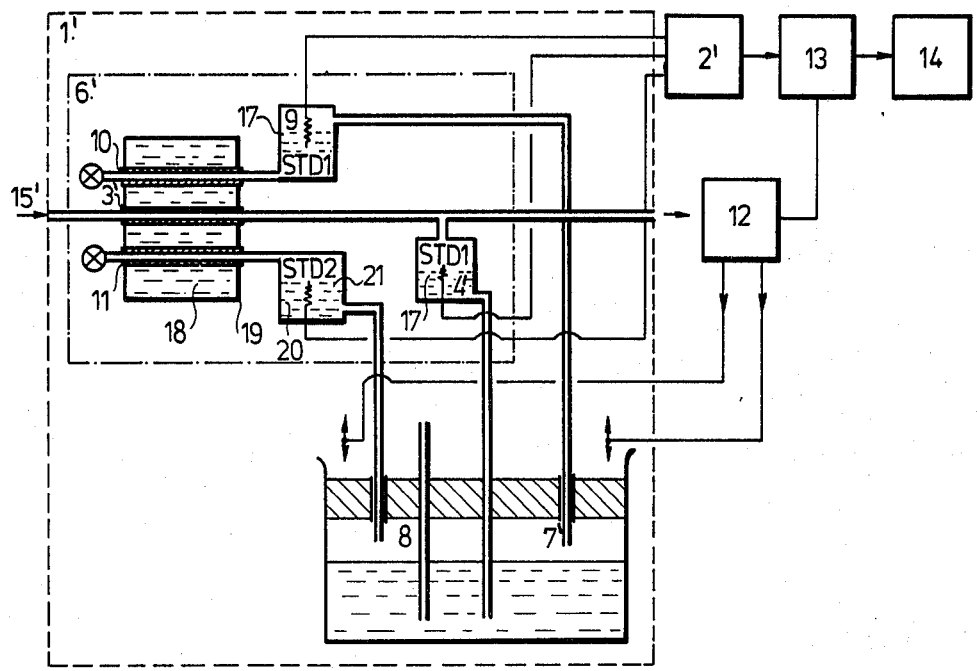
FIG. 2 shows an automatic fault compensation $Na^+$-ion concentration measuring apparatus with two fluid clutches.

FIG. 2 shows an automatic fault-compensation $Na^+$-ion concentration measuring equipment of a more complex construction, provided with two fluid clutches.

In FIG. 2 measuring cell 1' is connected to electronic signal processor 2' and control unit 12. In measuring chain 6' of measuring cell 1' sensing element 3' and sample-side reference electrode 4' are in contact with sample 15'. Besides the above mentioned sample-side sensing-element 3', integral sensing element 19 of measuring chain 6' comprises first standard-side and second standard-side sensing elements 10 and 11 in galvanic contact with sample-side sensing element 3' and with each other through electrolyte 18. First standard-side sensing element 10 and first standard-side reference electrode 9 are in galvanic contact through first standard solution 17. Similarly, second standard-side sensing element 11 and second standard-side reference electrode 20 are in galvanic contact through second standard solution 21. In addition to measuring chain 6' measuring cell 1' comprises fluid clutch 7' being in galvanic contact, through a liquid duct, with the liquid space of sample-side and first standard-side reference electrodes 4' and 9, as well as second fluid clutch 8 being in galvanic contact, through a liquid duct, with the liquid space of sample-side and second standard-side reference electrodes 4' and 20.

Measuring cell 1' is connected to electronic signal processor 2' through sample-side, first standard-side and second standard-side reference electrodes 4', 9 and 20 and control unit 12 through first and second fluid clutches 7' and 8; signal processor 2' and control unit 12 are connected to fault compensating unit 13, while the latter to arithmetic and display unit 14.

The simple pK measuring equipment provided with one fluid clutch, shown on FIG. 1, functions as follows:

Electronic signal processor 2 and measuring cell constitute 1—with the exception of liquid clutch 7 being a part of the latter—a traditional electro-analytical potentiometric measuring equipment and it does function in such way. The measuring signal depending on the parameter to be determined is the potential occurring on the surface between sample 15 and sensing-element 3. The electrode-potentials occurring on other elements of measuring chain 6—required only for the carrying out of the measurements in practice—i.e. on sample-side and sensing-element-side reference electrodes 4 and 5, are, however, elements producing—by their change—disturbing signals, measuring errors, not conveying useful information.

The errors resulting from the instability of reference potentials incurring on sample-side and sensing-element-side reference electrodes 4 and 5 are compensated as follows: the sensing surfaces of sensing element 3 are periodically short-circuited by means of fluid-clutch 7,—by this the potentials arising on the sensing surfaces between sample 15 and sensing element 3, i.e. internal electrolyte 16 and sensing element 3 are eliminated from the measuring chain. Thus sample-side reference electrode 4 is connected directly in series with sensing-element-side reference electrode 5 and their resultant potential is measured, then it is deducted from the value of potential obtained as a result of the previous "traditional" measurement performed without short-circuiting. The value of potential obtained in such way is still subject to the standard solution concentration to be measured, however, it does not depend on the electrode potential arising on one of the reference electrodes and thus on their changes resulting in measuring error either.

The pK value to be determined may be calculated from the cell-potential that can be measured in the in- and out position of fluid clutch 7, on the basis of the formula below.

$$pK_x = \frac{(U_x - U'_x) - (U_{STD\,1} - U'_{STD\,1})}{S} + pK_{STD}$$

in which:
$pK_x$ is the pK-value of sample 15 to be determined;
$pK_{STD}$ is the pK-value of standard solution used as internal electrolyte 16;
$U_x$ is the potential to be measured in out-position of fluid clutch 7, in the case where measuring cell 1 is charged with sample 15;
$U'_x$ is $U_x$ potential to be measured in the in-position of fluid clutch 7;
$U_{TSD\,1}$ is the potential measured in the "first matching spot" in the out-position of liquid clutch 7, when measuring cell 1 was charged with a first standard solution. It is advisable to use, when first matching is performed, a solution of a composition similar to that of internal electrolyte 16.

$U'_{STD1}$ is the $U_{STD1}$ potential measured in the in-position of liquid clutch 7.

S is the numerical value of the response-function slope characteristic of sensitivity of sensing element 3, determined at the time of matching in the second matching spot, by the traditional method.

It can be seen that in the formula the potentials of reference electrodes 4 and 5 are not figured in; they were eliminated in the course of the calculation. The required frequency of matching steps is determined only by the stability of two parameters—$U_{TSD1}$ and S—characteristic of sensing element 3.

Figure 3:
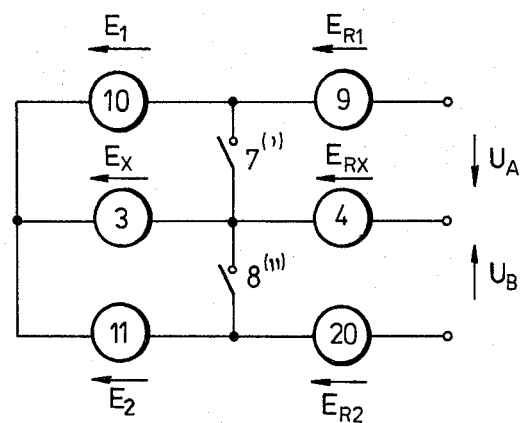
FIG. 3 is an equivalent circuit of the measuring cell of FIG. 2.

FIG. 3 facilitates the comprehension of the operational principle of the automatic fault-compensating $Na^+$-ion concentration measuring equipment of more complex construction provided with two fluid clutches, shown in FIG. 2., illustrating a simple electric diagram of measuring cell 1' of the measuring apparatus.

In a preferred embodiment according to the example measuring chain 6' placed in measuring cell 1' of the measuring apparatus has three "ends": sample-side 4', first standard-side and second standard-side reference electrodes 9 and 20. Besides the above reference electrodes, measuring chain 6' comprises so called integral sensing element 19. In this case the chemical and the mechanical condition of sample-side, first standard-side and second standard-side sensing elements 3', 10 and 11, as well as their construction, the standard potentials arising on them, the value of the response-function-slope characteristic of their sensitivity, i.e. their interim change, is nearly identical, then—measuring separately the potentials on two standard-side reference electrodes 9 and 10, as compared to sample-side reference electrode 4', the sample concentration—or its pNa value—can be calculated from the two potentials. The value obtained in such a way is practically independent from the standard potential of sensing elements 3', 10 and 11 and from the response-function-slope, consequently from their interim change resulting in measuring error. This calculated value, however, still depends on the reference potentials arising on reference electrodes 4', 9 and 20, thus, also on their instability. The resulting measuring errors can be eliminated by the application of first and second fluid clutches 7' and 8. In its "on" position, fluid clutch 7' short-circuits both sensing surfaces of sample-side and first standard-side sensing elements 3' and 10 and facilitates to measure directly the resultant of electrode potentials arising on sample-side and first standard-side reference electrodes 4' and 9. Similarly, second fluid clutch 8 short-circuits, in its "on" position, the sensing surfaces of sample-side and standard-side sensing elements 3' and 11, facilitating to measure directly the reresultant of electrode potentials arising on sample-side and second standard-side reference electrodes 4' and 20. Electronic signal processor 2' measures continuously two potentials $U_A$; $U_B$, arising on standard-side reference electrodes 9 and 20, as compared to sample-side reference electrode 4'. Control unit 12 short-circuits periodically e.g. by turns, at the end of each measurement, fluid clutch 7', then second fluid clutch 8. Fault compensating unit 13 produces the difference between potentials measured by electronic signal processor 2' in the "out" and "in" position of fluid clutches 7', 8.

Arithmetic and display unit 14 calculates, from the fault compensated "difference signals" and displays the wanted $Na^+$-ion concentration on the basis of the below formula:

$$c_x = \exp_{10} \frac{\lg c_1 /(U_{Bx} - U''_{Bx}) - (U_{B2} - U''_{B2})/ - \lg c_2/(U_{Ax} - U''_{Ax}) - (U_{A1} - U'_{A1})/}{/(U_{Bx} - U''_{Bx}) - (U_{B2} - U''_{B2})/ - /(U_{Ax} - U''_{Ax}) - (U_{A1} - U'_{A1})/}$$

in which:

$c_x$ is the $Na^+$-concentration of sample 15' to be determined;

$c_1$ is the $Na^+$-ion concentration of first standard-solution 17;

$c_2$ is the $Na^+$ ion concentration of second standard-solution 21;

$U_{Ax}$ is the potential to be measured between first standard-side and sample-side reference electrodes 9 and 4', when sensing element 3' is charged with sample 15' and first and second fluid clutches 7' and 8 are in the "out" position;

$U'_{Ax}$ is the $U_{Ax}$ potential to be measured in the "on" position of first fluid clutch 7';

$U_{A1}$ is the potential measured—when matching—between first standard-side and sample-side reference electrodes 9 and 4', when sensint element 3' was charged with first standard solution 7 and first and second fluid clutches 7' and 8 were in the "out" position or the first matching spot;

$U'_{A1}$ is the $U_{A1}$ potential measured in the "on" position of the first fluid clutch 7';

$U_{Bx}$ is the potential to be measured between second standard-side and sample-side reference electrodes 20 and 4', when sensing element 3' is charged with sample 15' and first and second fluid clutches 7' and 8 are in the "out" position;

$U''_{Bx}$ is the $U_{Bx}$ potential to be measured in the "on" position of second fluid clutch 8;

$U_{B2}$ is the potential measured—when matching—between second standard-side and sample-side reference electrodes 20 and 4', when sensing element 3' was charged with second standard-solution 21, and first and second fluid clutches 7' and 8 were in the "out" position or the second matching spot;

$U''_{B2}$ is the potential $U_{B2}$ measured in the "on" position of second fluid clutch 8.

The main advantages of the measuring process and apparatus according to the present invention may be summarized as follows:

elimination of disturbing signals arising on the elements of the measuring chain, not conveying useful information;

facilitating the control of the electro-chemical parameters of the sensing elements and reference electrodes during the measurement;

making of the result of measurement independent from the disturbing changes of the electro-chemical parameters of the sensing element;

by its application, matching in the course of the measurement can be performed;

elimination of the disturbing effect of flow potential;

by its application the error caused by diffusion potential can be decreased considerably;

it enables continuous or intermittently continuous measurements with considerably higher accuracy than up to now;

it may decrease considerably the total period required for the analysis;

by its application the required frequency of one- or two-spot matching may considerably be decreased;

elimination of the disturbing effect of long-lasting electronic drift of the measuring equipment.

What is claimed is:

1. In an electro-analytical measuring process wherein a measuring chain comprising at least one sensing element and reference electrodes is provided, the improvement comprising the steps of periodically galvanically short-circuiting at least one part of the measuring chain by a fluid clutch with an electrically conductive electrolyte and fault compensating the measuring signals obtained from the measuring chain when not short-circuiting with the measuring signals obtained during the short-circuiting thereof.

2. An electro-analytical measuring apparatus for the selective, rapid and high-precision determination of concentration, ion-activity of stationary or flowing solutions or of partial pressure of gases, comprising: a measuring cell and an electronic signal processor connected to the measuring cell, wherein the measuring cell comprises a measuring chain having at least one sensing element and reference electrodes and at least one means for galvanically short-circuiting at least one part of the measuring chain, the means comprising a fluid clutch having an electrically conductive electrolyte.

3. The apparatus according to claim 2, wherein the means further comprises a control unit connected to the measuring cell for periodically controlling the galvanic short-circuiting of at least one part of the measuring chain.

4. The apparatus according to claim 3, further comprising fault compensating means connected to the electronic signal processor and to control unit for producing at least one fault compensated signal from measuring signals obtained during the short-circuited and the non-short-circuited state of at least one part of the measuring chain.

5. The apparatus according to claim 4, further comprising arithmetic and display means connected to the output of the fault compensating means for calculating the numerical value of the parameter to be measured by utilizing the fault compensating signal.

* * * * *